(12) United States Patent
Inagawa et al.

(10) Patent No.: US 7,433,770 B2
(45) Date of Patent: Oct. 7, 2008

(54) HYDRAULIC FLUID CHANGE INDICATING DEVICE FOR AUTOMATIC TRANSMISSION

(75) Inventors: Yasushi Inagawa, Wako (JP);
Mitsumasa Furumoto, Wako (JP);
Hideo Koyama, Wako (JP); Yoshiari Takagi, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 719 days.

(21) Appl. No.: 11/002,701

(22) Filed: Dec. 3, 2004

(65) Prior Publication Data

US 2005/0131599 A1  Jun. 16, 2005

(30) Foreign Application Priority Data

Dec. 9, 2003 (JP) ............................. 2003-409828

(51) Int. Cl.
*G06F 7/00* (2006.01)

(52) U.S. Cl. ............................. 701/51; 701/29; 477/34; 477/37; 477/98; 307/152; 307/144

(58) Field of Classification Search ............... 477/176, 477/34, 37, 107, 45, 115, 926, 98, 120, 76; 72/351; 701/23, 29, 51, 300; 307/152, 144, 307/651; 475/1, 125, 163, 199, 254; 73/53.04, 73/54.16

See application file for complete search history.

(56) References Cited

U.S. PATENT DOCUMENTS 5,960,669 A * 10/1999 Ohashi et al. ................ 74/335
6,009,361 A * 12/1999 Huber et al. ................. 701/29
6,266,587 B1 * 7/2001 Guertler et al. .............. 701/30
6,543,397 B2 * 4/2003 Sandberg et al. .......... 123/41.15

FOREIGN PATENT DOCUMENTS

JP  62-93415  4/1987
JP  62-093415 * 4/1987

OTHER PUBLICATIONS

Jih-Jenn Huang; DeBra, D.B.; "Model predictive fluid temperature control for the quiet hydraulic precision turning machine" Sep. 15-18, 1996 pp. 486-491.*

* cited by examiner

*Primary Examiner*—Tuan C To
*Assistant Examiner*—Redhwan Mawari
(74) *Attorney, Agent, or Firm*—Westerman, Hattori, Daniels & Adrian, LLP.

(57) ABSTRACT

A hydraulic fluid change indicating device for an automatic transmission includes a first deterioration rate calculating unit; a deterioration acceleration coefficient calculating unit; and a thermal hydraulic fluid deterioration calculating unit for calculating a thermal hydraulic fluid deterioration according to the first deterioration rate and the deterioration acceleration coefficient. The device further includes a second deterioration rate calculating unit according to an engine speed, input shaft speed, and output shaft speed; a mechanical hydraulic fluid deterioration calculating unit for calculating a mechanical fluid deterioration according to the second deterioration rate; and a determining unit for determining whether or not the thermal hydraulic fluid deterioration or the mechanical hydraulic fluid deterioration is greater than a predetermined hydraulic fluid change threshold.

3 Claims, 6 Drawing Sheets

HYDRAULIC FLUID CHANGE INDICATING DEVICE FOR AUTOMATIC TRANSMISSION

BACKGROUND OF THE INVENTION

1. Field of the Invention

The present invention relates to a hydraulic fluid change indicating device for an automatic transmission for a vehicle which can suitably indicate a warning of changing a hydraulic fluid for the automatic transmission.

2. Description of the Related Art

An engine oil used for lubrication of an engine for a vehicle and a hydraulic fluid used for lubrication of a transmission deteriorate with the elapse of time. Therefore, it is necessary to change the engine oil and the hydraulic fluid for the transmission. For example, it is recommended in an operation manual to change the engine oil every time a fixed distance is traveled or a fixed period is passed. The time of such engine oil change is shown by attaching a label at an easy-to-see place. However, such a periodic change of engine oil is apt to be forgotten.

If the engine oil or the hydraulic fluid for the transmission is used beyond an allowable deterioration degree, such an excess use may interfere with a lubricating operation. Accordingly, it is important to show a warning of changing the engine oil or the hydraulic fluid. However, the deterioration of the engine oil or the hydraulic fluid is dependent not only on the distance traveled or the period of time elapsed, but also largely on the use condition of a vehicle such as a road condition. Therefore, it is unsuitable to warn on the basis of only the distance traveled or the period of time elapsed.

For example, Japanese Patent Publication No. Hei 6-39893 discloses a lubricating oil change warning device having a configuration such that predetermined lubricating oil deterioration coefficients according to vehicle speeds and the uses of a lubricating oil such as an engine oil are preliminarily stored, a corresponding one of the deterioration coefficients is read according to a vehicle speed detected by a sensor and the temperature of the lubricating oil detected by a sensor, the degree of deterioration of the lubricating oil is computed by using this deterioration coefficient, and a warning of changing the lubricating oil is output when this deterioration degree exceeds a predetermined value.

The lubricating oil change warning device described in the above publication is mainly adapted to the change time for an engine oil. That is, the lubricating oil is an engine oil, and the vehicle speed and the temperature of the engine oil are used as physical quantities changing according to a vehicle operating condition. However, it is unsuitable to directly apply this lubricating oil change warning device to a hydraulic fluid change warning device for an automatic transmission. That is, the automatic transmission includes a torque converter, so that there is a special circumstance that the deterioration of the hydraulic fluid is promoted by heat generation in the torque converter. Accordingly, if the lubricating oil change warning device described in the above publication is used as a hydraulic fluid change warning device for an automatic transmission, a suitable warning of changing the hydraulic fluid cannot be given because a parameter on the heat generation in the torque converter is not considered.

SUMMARY OF THE INVENTION

It is therefore an object of the present invention to provide a hydraulic fluid change indicating device for an automatic transmission for a vehicle which can suitably indicate a warning of changing a hydraulic fluid for the automatic transmission.

In accordance with an aspect of the present invention, there is provided a hydraulic fluid change indicating device for an automatic transmission for a vehicle, including fluid temperature detecting means for detecting the temperature of a hydraulic fluid for the automatic transmission; engine speed detecting means for detecting the rotational speed of an engine; input shaft speed detecting means for detecting the rotational speed of an input shaft in the automatic transmission; output shaft speed detecting means for detecting the rotational speed of an output shaft in the automatic transmission; heat amount detecting means for detecting the amount of heat generated in a torque converter; first deterioration rate calculating means for obtaining a first deterioration rate according to the fluid temperature detected by the fluid temperature detecting means; deterioration acceleration coefficient calculating means for obtaining a deterioration acceleration coefficient according to the heat amount detected by the heat amount detecting means; means for calculating a thermal hydraulic fluid deterioration according to the first deterioration rate and the deterioration acceleration coefficient; second deterioration rate calculating means for obtaining a second deterioration rate according to the engine speed, the input shaft speed, and the output shaft speed; means for calculating a mechanical hydraulic fluid deterioration according to the second deterioration rate; determining means for determining whether or not the thermal hydraulic fluid deterioration or the mechanical hydraulic fluid deterioration is greater than a predetermined hydraulic fluid change threshold; and indicating means for indicating a warning of changing the hydraulic fluid when the determining means determines that the thermal hydraulic fluid deterioration or the mechanical hydraulic fluid deterioration is greater than the hydraulic fluid change threshold.

According to this aspect, the amount of heat generated in the torque converter of the automatic transmission is calculated, and the thermal deterioration rate based on the fluid temperature is corrected according to the heat amount calculated above. Accordingly, the accuracy of detection of the change time for the hydraulic fluid can be improved.

In accordance with another aspect of the present invention, the hydraulic fluid change indicating device further includes storing means for storing the result of determination showing a warning of changing the hydraulic fluid; and second determining means for determining whether or not an engine oil is to be changed. When the time of changing of the engine oil is determined by the second determining means, the determination result stored in the storing means is read to indicate the warning of changing the hydraulic fluid by the indicating means.

According to this aspect, the determination result showing a warning of changing the hydraulic fluid is previously stored into the storing means. At the time of changing of the engine oil, the determination result stored in the storing means is read to indicate the warning of changing the hydraulic fluid by the indicating means. Accordingly, the change of the engine oil and the change of the hydraulic fluid for the automatic transmission can be performed at the same time.

In accordance with a further aspect of the present invention, the hydraulic fluid change threshold is set so that the distance corresponding to the remaining service life of the hydraulic fluid is greater than the average of the past change distances for the engine oil and less than the value twice the average.

According to this aspect, the hydraulic fluid change threshold is set in consideration of the distance corresponding to the remaining service life of the hydraulic fluid. Accordingly, the change of the engine oil and the change of the hydraulic fluid can be performed simultaneously before the service life of the hydraulic fluid is ended, thereby improving the maintainability.

The above and other objects, features and advantages of the present invention and the manner of realizing them will become more apparent, and the invention itself will best be understood from a study of the following description and appended claims with reference to the attached drawings showing some preferred embodiments of the invention.

DETAILED DESCRIPTION OF THE PREFERRED EMBODIMENTS

Figure 1:
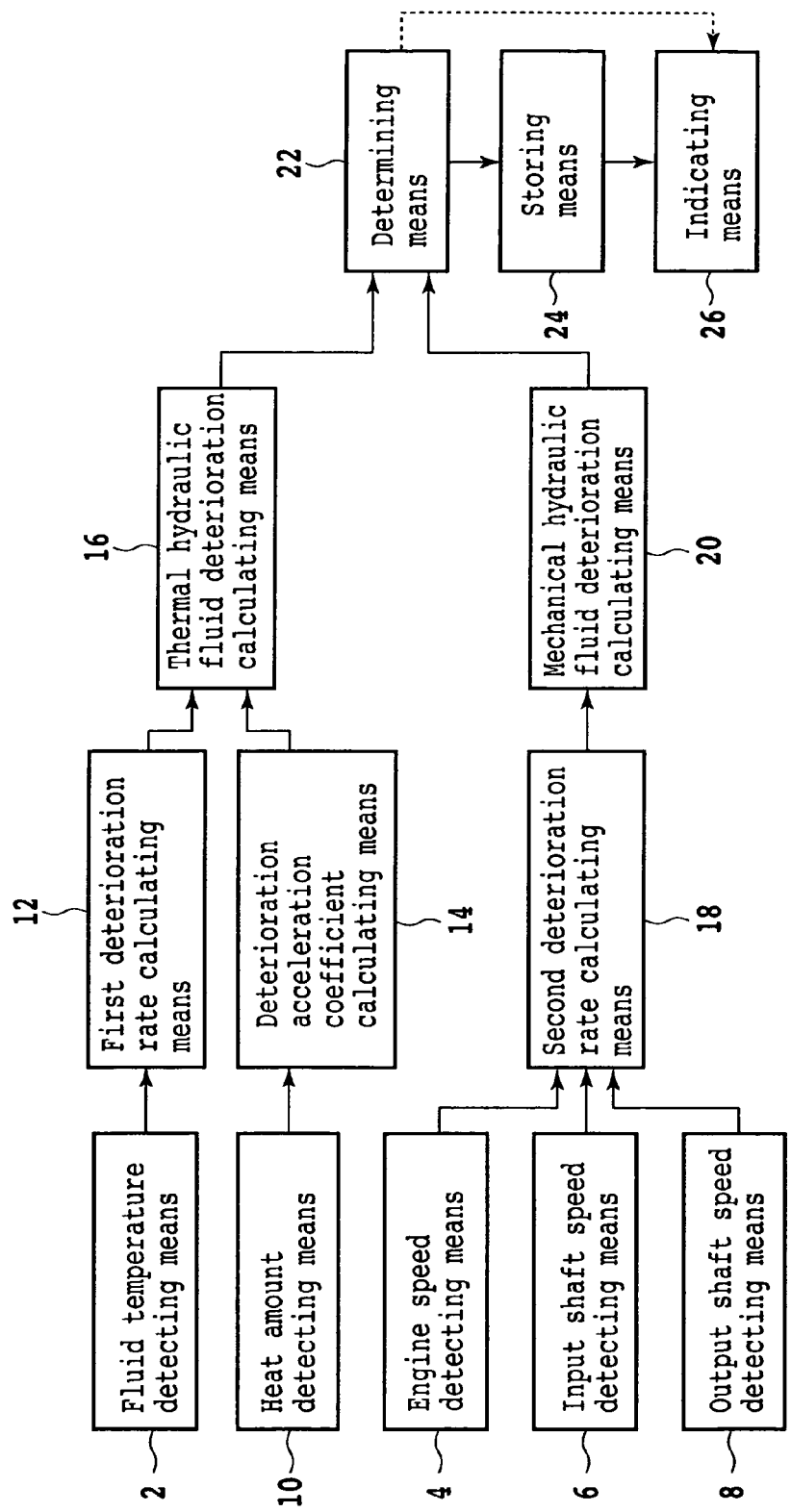
FIG. 1 is a block diagram showing a basic configuration of the present invention.

FIG. 1 is a block diagram showing a basic configuration of the present invention. The hydraulic fluid change indicating device for the automatic transmission according to the present invention includes fluid temperature detecting means 2 for detecting the temperature of a hydraulic fluid for the automatic transmission, engine speed detecting means 4 for detecting the rotational speed of an engine, input shaft speed detecting means 6 for detecting the rotational speed of an input shaft in the automatic transmission, output shaft speed detecting means 8, and heat amount detecting means 10 for detecting the amount of heat generated in a torque converter.

A first deterioration rate is obtained by first deterioration rate calculating means 12 according to the fluid temperature detected by the fluid temperature detecting means 2. A deterioration acceleration coefficient is obtained by deterioration acceleration coefficient calculating means 14 according to the heat amount detected by the heat amount detecting means 10. A thermal hydraulic fluid deterioration is calculated by thermal hydraulic fluid deterioration calculating means 16 according to the first deterioration rate and the deterioration acceleration coefficient.

On the other hand, a second deterioration rate is obtained by second deterioration rate calculating means 18 according to the engine speed, the input shaft speed, and the output shaft speed. A mechanical hydraulic fluid deterioration is calculated by mechanical hydraulic fluid deterioration calculating means 20 according to the second deterioration rate. It is determined whether or not the thermal hydraulic fluid deterioration or the mechanical hydraulic fluid deterioration is greater than a predetermined hydraulic fluid change threshold by determining means 22. When the thermal hydraulic fluid deterioration or the mechanical hydraulic fluid deterioration is greater than the hydraulic fluid change threshold, a warning of changing the hydraulic fluid is indicated by indicating means 26.

Preferably, the result of determination showing the change of the hydraulic fluid is stored by storing means 24. When second determining means provided independently of the determining means 22 determines the time for changing of an engine oil, the determination result stored in the storing means 24 is read out to indicate the warning of changing the hydraulic fluid on the indicating means 26. Accordingly, the change of the engine oil and the change of the hydraulic fluid for the automatic transmission can be performed at the same time. The indicating means 26 may be realized by utilizing various meters provided on an instrument panel to turn on a lamp or the like.

Figure 2:
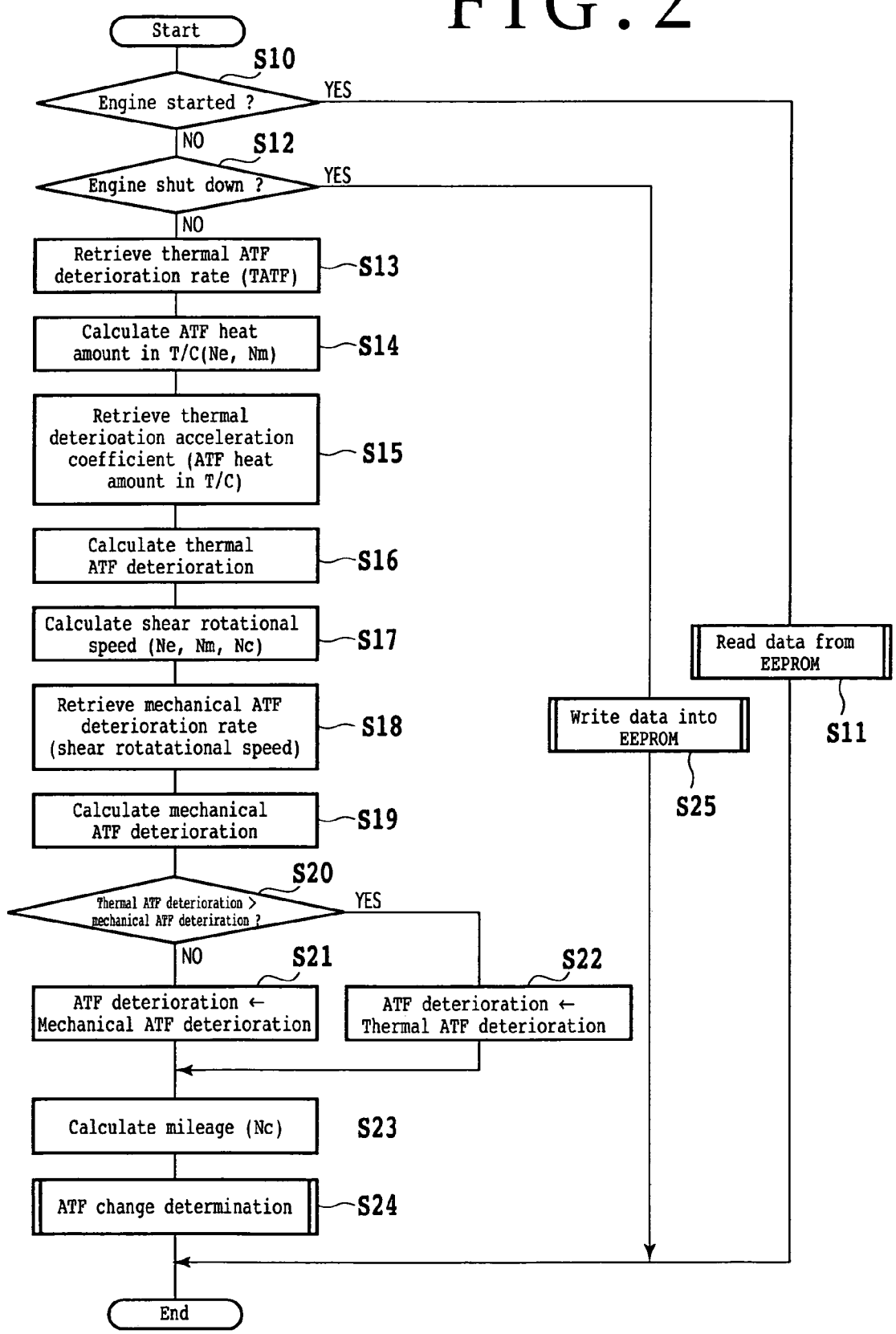
FIG. 2 is a flowchart showing a program for determining hydraulic oil change according to a preferred embodiment of the present invention.
Figure 6:
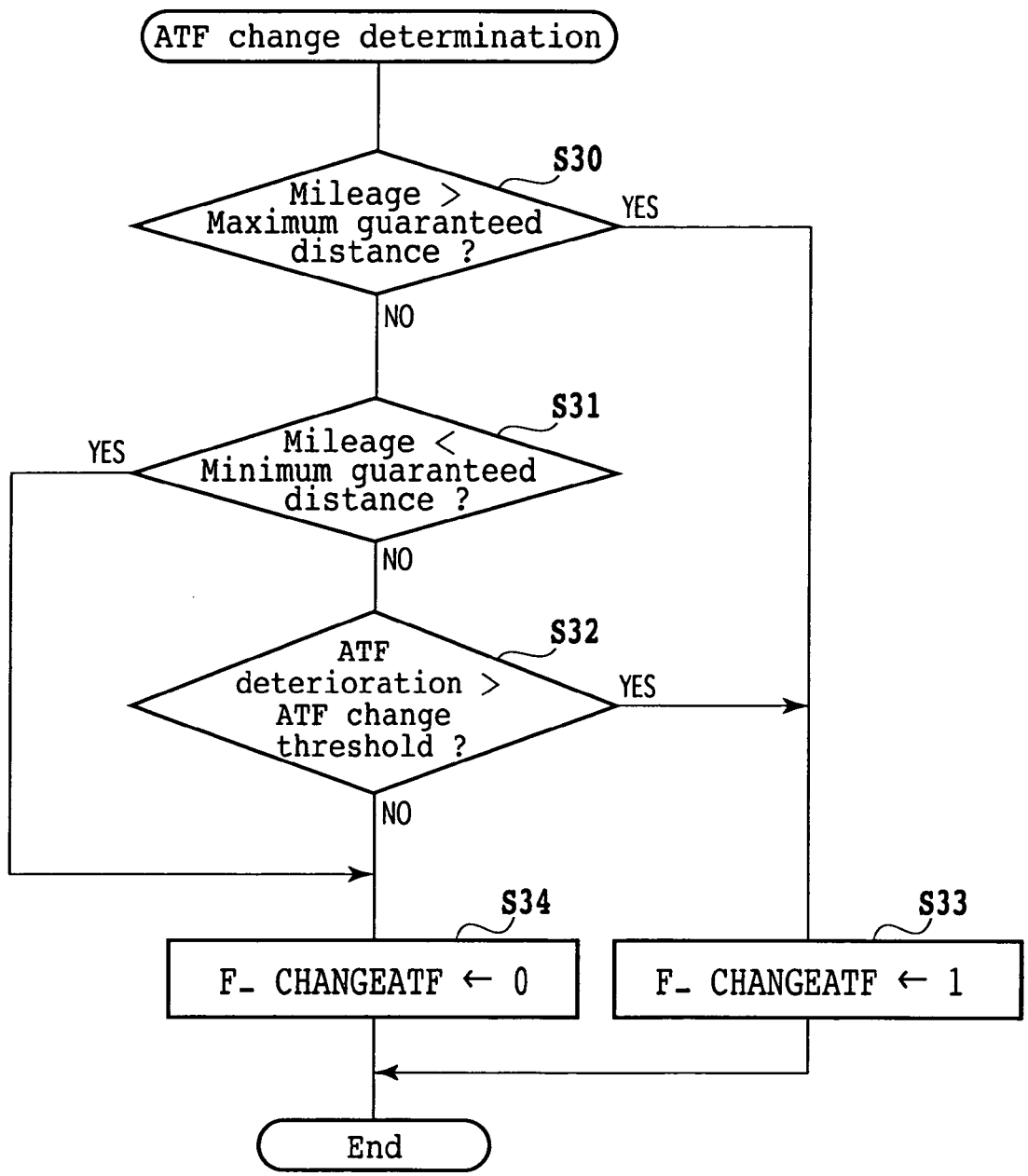
FIG. 6 is a flowchart showing the ATF change determination step.

The operation of this preferred embodiment will now be described with reference to the flowcharts shown in FIGS. 2 and 6. In step S10, it is determined whether or not the engine has been started, i.e., whether or not an ignition switch has been turned on. Just after the engine has been started, the answer in step S10 becomes YES, whereas this answer becomes NO at the next time and later. If the answer in step S10 is YES, the program proceeds to step S11 to read data stored in EEPROM as a nonvolatile memory. If the answer in step S10 is NO, the program proceeds to step S12 to determine whether or not the engine has been shut down.

Figure 3:
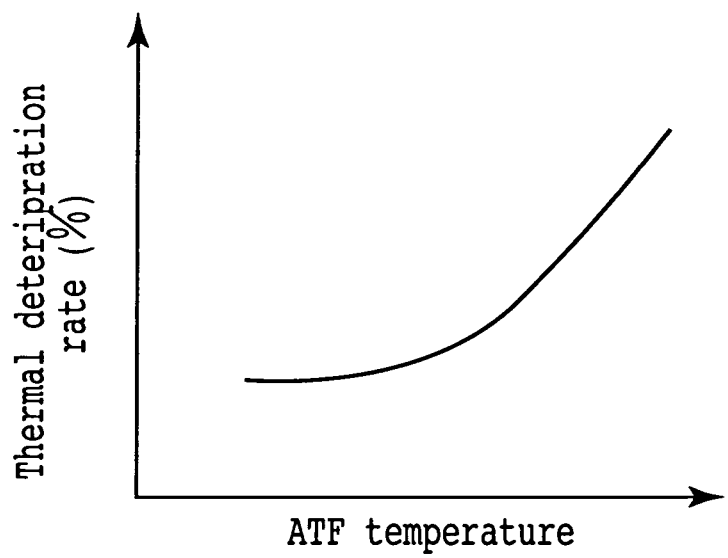
FIG. 3 is a table showing the relation between ATF temperature and thermal deterioration rate.

If the engine has not been shut down, i.e., if the engine is in operation, the program proceeds to step S13 to retrieve a thermal ATF (hydraulic fluid) deterioration rate (TATF). As shown in FIG. 3, the thermal ATF deterioration rate changes according to the temperature of the hydraulic fluid for the automatic transmission. This fluid temperature is detected by a fluid temperature sensor. The program next proceeds to step S14 to calculate the amount of heat generated from the ATF in the torque converter (T/C). The ATF heat amount DQOILTC in the torque converter is expressed as follows:

$$DQOILTC = TQIN \times Ne - TQOUT \times Nm$$

where TQIN is the T/C pump absorption torque (input torque), TQOUT is the T/C turbine torque (output torque), Ne is the rotational speed of the engine, and Nm is the rotational speed of the input shaft in the automatic transmission.

Further, $$TQIN = \tau \times (Ne/1000)^2 \text{ and } TQOUT = k \times (TQIN)$$

Where $\tau$ is the T/C pump absorption torque coefficient and k is the T/C torque ratio. Accordingly, DQOILTC can be expressed as follows:

$$DQOILTC = TQIN(Ne - k \times Nm) = \tau \times (Ne/1000)^2 \times (Ne - k \times Nm)$$

Figure 4:
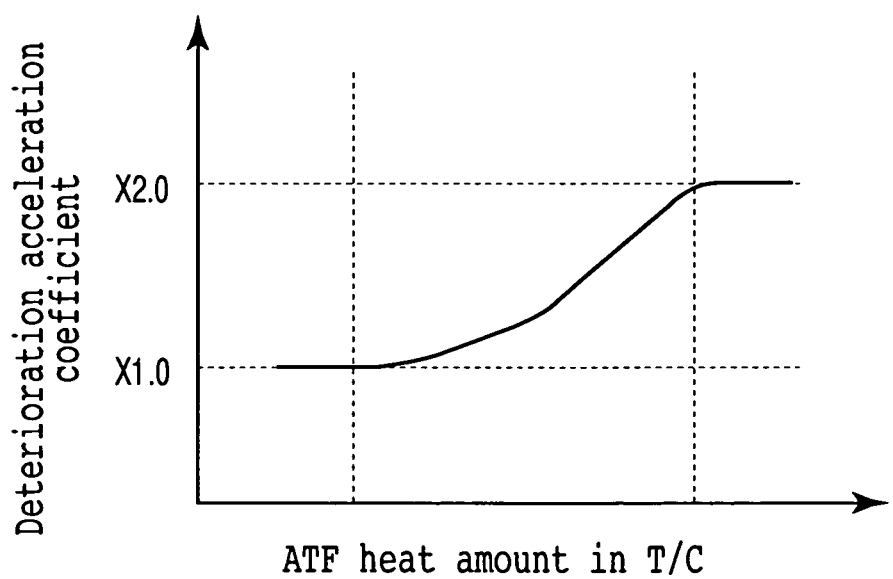
FIG. 4 is a table showing the relation between ATF heat amount in a torque converter and deterioration acceleration coefficient.

The program next proceeds to step S15 to retrieve a thermal deterioration acceleration coefficient according to the ATF heat amount in the torque converter. This thermal deterioration acceleration coefficient is retrieved from the table shown in FIG. 4, for example. The program next proceeds to step S16 to calculate a thermal ATF deterioration. This thermal ATF deterioration can be obtained by integrating the product of the thermal deterioration rate and the thermal deterioration acceleration coefficient with respect to time. In other words, assuming that the operation period of a thermal ATF deterioration estimating logic is one second, the thermal ATF deterioration can be obtained by integrating the thermal deterioration rate per second.

The program next proceeds to step S17 to calculate a shear rotational speed according to the rotational speed Ne of the engine, the rotational speed Nm of the input shaft in the automatic transmission, and the rotational speed Nc of the output shaft in the automatic transmission. More specifically, the shear rotational speed is given by:

Shear rotational speed=$Ne \times K1 + Nm \times K2 + Nc \times K3$ where K1, K2, and K3 are the coefficients for correcting the degree of influence on the mechanical deterioration to the respective rotating members. These coefficients K1, K2, and K3 are set according to the number of gear teeth at each rotating member and the number of bearings, for example.

Figure 5:
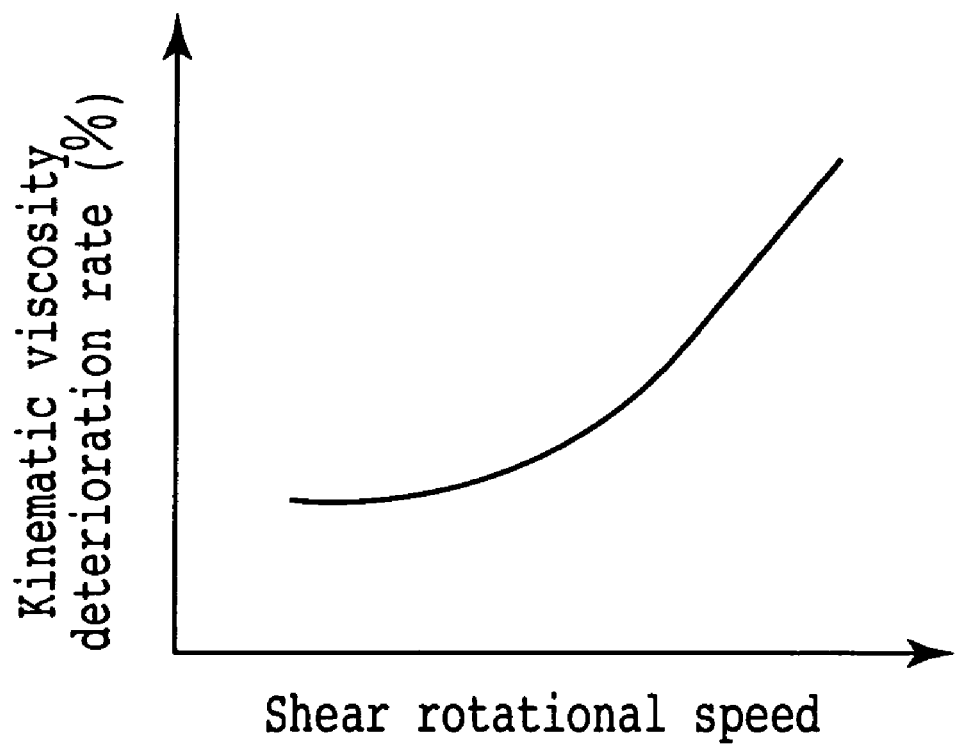
FIG. 5 is a table showing the relation between shear rotational speed and mechanical ATF deterioration rate (kinematic viscosity deterioration rate)

The program next proceeds to step S18 to retrieve a mechanical ATF deterioration rate according to the shear rotational speed. This mechanical ATF deterioration rate can be obtained by retrieving the table shown in FIG. 5, for example. The program next proceeds to step S19 to calculate a mechanical ATF deterioration. Assuming that the operation period of a mechanical ATF deterioration estimating logic is one second, the mechanical ATF deterioration can be obtained by integrating the mechanical deterioration rate per second.

In step S20, it is determined whether or not the thermal ATF deterioration is greater than the mechanical ATF deterioration. If the answer in step S20 is NO, the program proceeds to step S21 to adopt the mechanical ATF deterioration as the ATF deterioration. If the answer in step S20 is YES, the program proceeds to step S22 to adopt the thermal ATF deterioration as the ATF deterioration. The program next proceeds to step S23 to calculate a mileage (distance traveled) according to the rotational speed Nc of the output shaft in the automatic transmission. The mileage is given by:

Mileage=(Vehicle speed)×(Time)

Further, the vehicle speed is given by:

Vehicle speed=(Tire rotational speed per unit time)× (Distance traveled per tire rotation)=$(Nc \times RATIO) \times (2\pi \times RTIRE)$ where RATIO is the final gear ratio, and RTIRE is the tire radius. Accordingly, the mileage can be calculated by integrating the vehicle speed (distance traveled per second).

After the mileage is calculated in step S23, ATF change determination is executed in step S24. The ATF change determination is configured by the flowchart shown in FIG. 6. If it is determined that the engine has been shut down in step S12, the program proceeds to step S25 to write data into the EEPROM and is next ended. In the flowchart shown in FIG. 2, the steps S13 to S16 correspond to the thermal ATF deterioration estimating processing, the steps S17 to S19 correspond to the mechanical ATF deterioration estimating processing, and the steps S20 to S22 correspond to the ATF deterioration estimating processing.

The ATF change determination will now be described with reference to the flowchart shown in FIG. 6. In step S30, it is determined whether or not the mileage is greater than a maximum guaranteed distance. If the answer in step S30 is NO, the program proceeds to step S31 to determine whether or not the mileage is less than a minimum guaranteed distance. If the answer in step S31 is NO, the program proceeds to step S32 to determine whether or not the ATF deterioration is greater than an ATF change threshold. If the ATF deterioration is greater than the ATF change threshold, the program proceeds to step S33 to set an ATF change flag and to indicate an ATF change warning in one of various meters provided on an instrument panel, for example. If the answer in step S32 is NO, 0 is substituted into the bit of the ATF change flag (step S34), and this program is next ended.

If the answer in step S30 is YES, the program proceeds to step S33 to set the ATF change flag (i.e., substitute 1 into the flag bit) and to indicate the ATF change warning in one of the meters. If the answer in step S31 is YES, the program proceeds to step S34 to substitute 0 into the bit of the ATF change flag (step S34) and is then ended.

The flow of the hydraulic fluid (ATF) change determination for the automatic transmission has been described with reference to the flowcharts shown in FIGS. 2 and 6. The change time for the automatic transmission hydraulic fluid (ATF) may also be indicated in synchronism with the indication by indicating means for indicating the change time for the engine oil. More specifically, although the change time for the automatic transmission hydraulic fluid has been determined, the indication of the change time for the automatic transmission hydraulic fluid is delayed until the next change time for the engine oil, and the determination result is stored into a memory in an ECU. When the next change time for the engine oil has come, the determination result stored in the memory is read to indicate the ATF change warning and the engine oil change warning at the same time.

In a service shop or the like for the vehicle, the ECU can be accessed to check the determination result stored in the memory. Accordingly, the automatic transmission hydraulic fluid can be changed with suitable timing by checking the determination result. For example, it is possible to eliminate such an inconvenience that the automatic transmission hydraulic fluid is to be changed on the next day after the engine oil has been changed (or vice versa). Thus, it becomes unnecessary for the user to take the vehicle to the service shop many times for the ATF change and the engine oil change.

Figure 7:
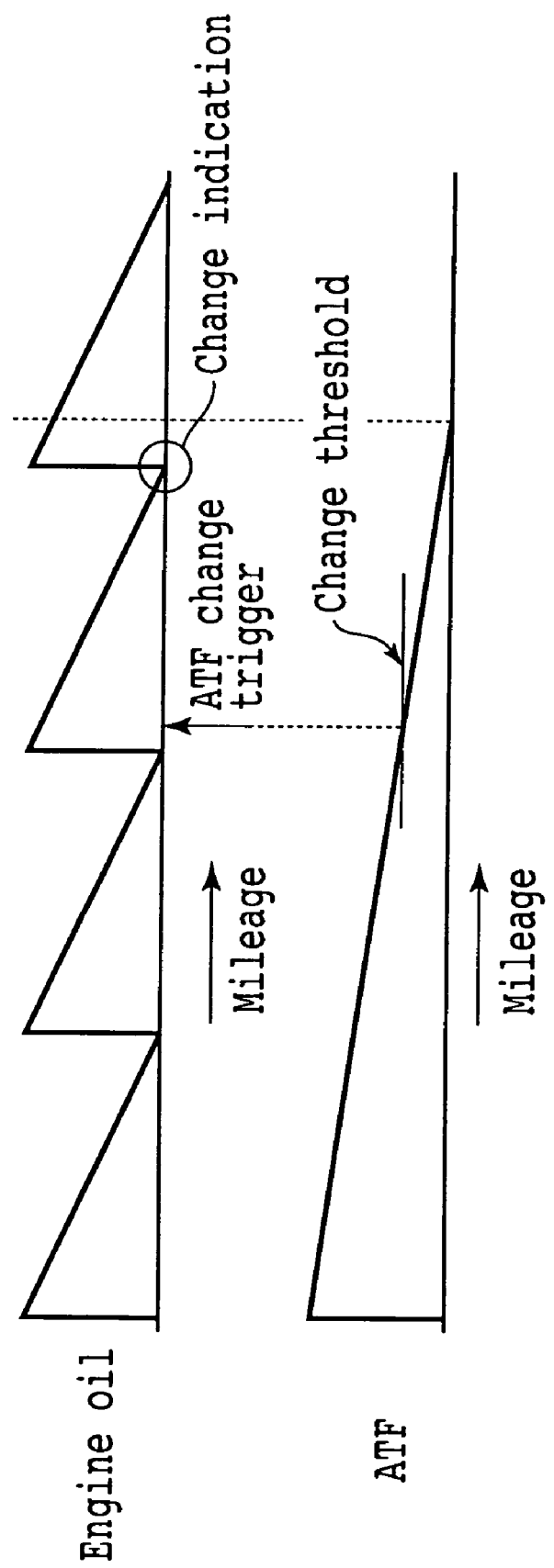
FIG. 7 is a graph for illustrating another preferred embodiment wherein the change of engine oil and the change of ATF are linked.

Further, the engine oil change and the ATF change may be linked in the following manner. More specifically, the next change distance (time) for the engine oil is predicted from the average of the past change cycles (distances) for the engine oil. By using this predicted change time for the engine oil, the ATF change and the engine oil change are synchronized. For example, FIG. 7 shows the relation between the ATF change time and the engine oil change time, wherein the horizontal axis represents mileage, and the vertical axis represents the remaining service life of the engine oil or the ATF. The ATF change threshold is set so as to satisfy the following relation.

Average of past change distances for engine oil<Distance corresponding to remaining service life of ATF<(Average of past change distances for engine oil)×2

When the ATF deterioration exceeds this ATF change threshold, the determination result is stored as an ATF change trigger into the memory. At the next change time for the engine oil, the determination result is read from the memory and the ATF change warning is indicated together with the engine oil change warning. By suitably setting the ATF change threshold as mentioned above, the engine oil change and the ATF change can be performed simultaneously before the ATF is completely deteriorated.

The present invention is not limited to the details of the above described preferred embodiments. The scope of the invention is defined by the appended claims and all changes and modifications as fall within the equivalence of the scope of the claims are therefore to be embraced by the invention.

What is claimed is:

1. A hydraulic fluid change indicating device for an automatic transmission for a vehicle, comprising:

fluid temperature detecting means for detecting the temperature of a hydraulic fluid for said automatic transmission;
engine speed detecting means for detecting the rotational speed of an engine;
input shaft speed detecting means for detecting the rotational speed of an input shaft in said automatic transmission;
output shaft speed detecting means for detecting the rotational speed of an output shaft in said automatic transmission;
heat amount detecting means for detecting the amount of heat generated in a torque converter;
first deterioration rate calculating means for obtaining a first deterioration rate according to the temperature of the hydraulic fluid for said automatic transmission detected by said fluid temperature detecting means;
deterioration acceleration coefficient calculating means for obtaining a deterioration acceleration coefficient according to the amount of heat generated in said torque converter detected by said heat amount detecting means;
means for calculating a thermal hydraulic fluid deterioration according to said first deterioration rate and said deterioration acceleration coefficient;
second deterioration rate calculating means for obtaining a second deterioration rate according to the rotational speed of said engine, the rotational speed of said input shaft in said automatic transmission, and the rotational speed of said output shaft in said automatic transmission;
means for calculating a mechanical hydraulic fluid deterioration according to said second deterioration rate;
determining means for determining whether a greater one of said thermal hydraulic fluid deterioration or said mechanical hydraulic fluid deterioration is greater than a predetermined hydraulic fluid change threshold; and
indicating means for indicating a warning to change said hydraulic fluid when said determining means determines that said greater of said thermal hydraulic fluid deterioration or said mechanical hydraulic fluid deterioration is greater than said hydraulic fluid change threshold.

2. The hydraulic fluid change indicating device for an automatic transmission for a vehicle according to claim 1, further comprising:
storing means for storing a result of a determination showing said warning to change said hydraulic fluid; and
a second determining means for determining whether or not an engine oil is to be changed;
wherein when a time of changing of said engine oil is determined by said second determining means, said determination result showing said warning to change said hydraulic fluid stored in said storing means is read to indicate said warning to change said hydraulic fluid by said indicating means.

3. The hydraulic fluid change indicating device for an automatic transmission for a vehicle according to claim 2, wherein said hydraulic fluid change threshold is set so that a distance corresponding to a remaining service life of said hydraulic fluid is greater than an average of past change distances for said engine oil and less than a value twice said average.

* * * * *